(12) United States Patent
Jin et al.

(10) Patent No.: US 11,815,788 B2
(45) Date of Patent: Nov. 14, 2023

(54) PHENOTYPING IMAGING SYSTEM WITH AUTOMATIC LEAF-HANDLING MECHANISM

(71) Applicant: Purdue Research Foundation, West Lafayette, IN (US)

(72) Inventors: Jian Jin, West Lafayette, IN (US); Liangju Wang, Beijing (CN); Jialei Wang, Tulsa, OK (US); Yikai Li, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/736,758

(22) Filed: May 4, 2022

(65) Prior Publication Data
US 2022/0357634 A1 Nov. 10, 2022

Related U.S. Application Data

(60) Provisional application No. 63/183,637, filed on May 4, 2021.

(51) Int. Cl.
*G03B 15/03* (2021.01)
*H04N 23/74* (2023.01)
*H04N 23/50* (2023.01)

(52) U.S. Cl.
CPC ............ *G03B 15/03* (2013.01); *H04N 23/50* (2023.01); *H04N 23/74* (2023.01)

(58) Field of Classification Search
CPC ............ G03B 15/03; G01J 2003/1204; G01J 3/0237; G01J 3/0278; G01J 3/0291;
(Continued)

(56) References Cited

U.S. PATENT DOCUMENTS 3,910,701 A 10/1975 Henerson et al.
7,660,698 B1 2/2010 Seelig et al.
(Continued)

FOREIGN PATENT DOCUMENTS

CN 103824113 A * 5/2014
CN 105717115 A * 6/2016
(Continued)

OTHER PUBLICATIONS

Adão et al., (2017). Hyperspectral Imaging: A Review on UAV-Based Sensors, Data Processing and Applications for Agriculture and Forestry. Remote Sens. 9, 1110:1-30.
(Continued)

*Primary Examiner* — Kathleen M Walsh
(74) *Attorney, Agent, or Firm* — Piroozi-IP, LLC (57) ABSTRACT

A method and system are disclosed for providing consistent images of leaves of plants, including articulating a lower case of a housing with respect to an upper case via an imaging chamber articulation mechanism from i) a closed state to ii) an open state, the articulable space forms an imaging chamber which is dark when the imaging chamber articulation mechanism is in the closed state, placing the leaf within the imaging chamber, articulating the imaging chamber articulation mechanism to the closed state, activating one or more light sources, actuating a linear actuator to thereby linearly move a camera from i) an initial position to ii) an end position, obtaining images from the camera, re-actuating the linear actuator to thereby linearly move the camera from the end position to the initial position, re-articulating the lower case to the open state, and removing the leaf.

18 Claims, 8 Drawing Sheets

(58) Field of Classification Search
CPC .. G01J 3/18; G01J 3/2823; G01N 2021/8466; G01N 21/31; G01N 33/0098; G06V 20/60; H04N 23/50; H04N 23/51; H04N 23/56; H04N 23/57; H04N 23/695; H04N 23/74
USPC .......................................................... 348/61
See application file for complete search history.

(56) References Cited

U.S. PATENT DOCUMENTS

| | | | |
|---|---|---|---|
| 2002/0090127 | A1 | 1/2002 | Wetzel et al. |
| 2004/0130714 | A1 | 7/2004 | Gellerman et al. |
| 2010/0111369 | A1 | 5/2010 | Lussier |
| 2010/0275691 | A1* | 11/2010 | Roberts ................ G01N 29/262 73/622 |
| 2011/0116688 | A1* | 5/2011 | Li ........................ G01N 33/0098 382/110 |
| 2018/0276818 | A1* | 9/2018 | Vander Velden .... H04N 23/681 |

FOREIGN PATENT DOCUMENTS

| | | | | |
|---|---|---|---|---|
| CN | 106596570 | A | * | 4/2017 |
| CN | 107869962 | A | * | 4/2018 |
| CN | 110296992 | A | * | 10/2019 |
| CN | 111193845 | A | * | 5/2020 ............. G01N 21/01 |
| JP | 2002170099 | A | * | 6/2002 |
| KR | 101619834 | B1 | * | 5/2016 |
| KR | 102059357 | B1 | * | 12/2019 ............. G01N 21/01 |
| WO | 2016051272 | A1 | | 4/2016 |
| WO | 2018195065 | A1 | | 10/2018 |

OTHER PUBLICATIONS

Suomalainen et al., (2014). A Lightweight Hyperspectral Mapping System and Photogrammetric Processing Chain for Unmanned Aerial Vehicles. Remote Sens., 6:11013-11030.
Ge et al., (2019). High-throughput analysis of leaf physiological and chemical traits with VIS-NIR-SWIR spectroscopy: a case study with a maize diversity panel. Plant Methods, 15:66:1-12.
Yang et al., (2018). Compact orthogonal-dispersion device using a prism and a transmission grating. Journal of the European Optical Society-Rapid Publications, 14:8:1-7.
Zhang et al., (2016). Development of a Near Ground Remote Sensing System. Sensors 16, 648:1-14.
Chen et al., (2018). Experimental Demonstration of Remote and Compact Imaging Spectrometer Based on Mobile Devices. Sensors 18, 1989:1-10.
Wang et al., (2020). LeafSpec: An accurate and portable hyperspectral corn leaf imager. Computers and Electronics in Agriculture, 169:1-11.
Addo-Quaye et al., (Mar. 2018). Whole-Genome Sequence Is Improved by Replication in a Population of Mutagenized Sorghum. G3:Genes, Genomes, Genetics, 8:1079-1094.
Bouchet et al., (Jun. 2017). Increased Power To Dissect Adaptive Traits in Global Sorghum Diversity Using a Nested Association Mapping Population. Genetics, 206: 573-585.
Chen et al., (2016). Genetic improvement in density and nitrogen stress tolerance traits over 38 years of commercial maize hybrid release. Field Crop Research, 196:438-451.
Elias et al., (2016). Half a Century of Studying Genotype X Environment Interactions in Plant Breeding Experiments. Crop Sci., 56:2090-2105.
Lin et al., (2012). Parallel domestication of the Shattering1 genes in cereals. Nature Genetics, 44(6):720-724.
International Search Report and Written Opinion issued by the Korean Intellectual Property Office, dated Jul. 31, 2018, or International Application No. PCT/US2018/027953; 17 pages.
International Preliminary Report on Patentability issued by The International Bureau of WIPO, Geneva, Switzerland, dated Oct. 22, 2019, for International Application No. PCT/US2018/027953; 15 pages.
Ge et al., (2016). Temporal dynamics of maize plant growth, water use, and leaf water content using automated high throughput RGB and hyperspectral imaging. Computers and Electronics in Agriculture, 127:625-632.
Gowen et al., (2007). Hyperspectral imaging—an emerging process analytical tool for food quality and safety control. Trends in Food Science and Technology, 18(12):590-598.
Li et al., (2014). A Review of Imaging Techniques for Plant Phenotyping. In Sensors, 14(11).
Virrlet et al., (2017). Field Scanalyzer: An automated robotic field phenotyping platform for detailed crop monitoring. Functional Plant Biology, 44(1):143-153.
Li et al., (Oct. 2013). Review of spectral imaging technology in biomedical engineering: achievements and challenges. Journal of Biomedical Optics 18(10), 100901.
Goetz et al., (2009). Three decades of hyperspectral remote sensing of the Earth: A personal view. Remote Sensing of Environment, 113:S5-S16.
Jacquemoud et al., (2009). PROSPECT+SAIL models: A review of use for vegetation characterization. Remote Sensing of Environment 113:S56-S66.
Zarco-Tejada et al., (2012). Fluorescence, temperature and narrow-band indices acquired from a UAV platform for water stress detection using a micro-hyperspectral imager and a thermal camera. Remote Sensing of Environment, 117:322-337.
Gutiérrez et al., (2019). Ground based hyperspectral imaging for extensive mango yield estimation. Computers and Electronics in Agriculture, 157:126-135.
Viggneau et al., (2011). Potential of field hyperspectral imaging as a non destructive method to assess leaf nitrogen content in Wheat. Field Crops Research, 122:25-31.
Xue et al., (2017). Significant Remote Sensing Vegetation Indices: A Review of Developments and Applications. Journal of Sensors 2017: 1-17.
Yuan et al., (May 2016). Optimal Leaf Positions for SPAD Meter Measurement in Rice. Frontiers in Plant Science, 7:1-10.
Gutiérrez et al., (Jul. 2018). On-The-Go Hyperspectral Imaging Under Field Conditions and Machine Learning for the Classification of Grapevine Varieties. Frontiers in Plant Science, 9:1-11.
Pandey et al., (Aug. 2017). High Throughput In vivo Analysis of Plant Leaf Chemical Properties Using Hyperspectral Imaging. Frontiers in Plant Science, 8:1-12.
Ward et al., (Oct. 1999). Gray Leaf Spot: A Disease of Global Importance in Maize Production. Plant Disease, 83(10):884-895.
Bareth et al., (Feb. 2015). Low-weight and UAV-based Hyperspectral Full-frame Cameras for Monitoring Crops: Spectral Comparison with Portable Spectroradiometer Measurements. PFG 1:69-79.
Chen et al., (Nov. 2014). Identification of Nitrogen, Phosphorus, and Potassium Deficiencies in Rice Based on Static Scanning Technology and Hierarchical Identification Method. PLoS ONE 9(11):1-1.

* cited by examiner

PHENOTYPING IMAGING SYSTEM WITH AUTOMATIC LEAF-HANDLING MECHANISM

CROSS-REFERENCE TO RELATED APPLICATIONS

The present patent application is related to and claims the priority benefit of U.S. Provisional Patent Application Ser. No. 63/183,637, filed May 4, 2021, entitled Phenotyping System, the contents of which are hereby incorporated by reference in its entirety into the present disclosure.

STATEMENT REGARDING GOVERNMENT FUNDING

This present disclosure was not supported by government funding.

TECHNICAL FIELD

The present disclosure generally relates to plant phenotypic systems, and in particular to a plant phenotyping imaging system with an automatic leaf-handling mechanism.

BACKGROUND

This section introduces aspects that may help facilitate a better understanding of the disclosure. Accordingly, these statements are to be read in this light and are not to be understood as admissions about what is or is not prior art.

A high throughput plant phenotyping system is required for plant researchers and precision agriculture in order improve high yields and also develop new genotype as well as to monitor plant health. Specifically, precision agriculture is now ubiquitously used to optimize crop yield especially in light of decades-long drought conditions in vast areas of the country by using systems with feedback to provide water where needed, improve monitoring of crop health, and minimizing environmental impact by optimizing fertilizers and insecticides to only area where these potentially harmful chemicals are deemed to be necessary. Furthermore, where new plants are being planted, it is necessary to understand and quantify plant growth and structure at a large scale.

In order to accurately quantify phenotyping over small and large areas, hyperspectral or multispectral imaging systems have been used to image plants in close range. Such systems require large human interaction. For example, a person taking these images needs to manipulate a leaf and the plant to improve image quality. However, by human intervention, significant error is introduced by way of varying levels of leaf and plant manipulation and inconsistency. Suppose a particular type of plant requires a certain angle with respect to lens of the image system to obtain the most amount of information. Human interactions inherently introduces inconsistencies that can result in reduced imaging quality. Additionally, different plants have different leaves with varying levels of toughness. Some plant leaves are easily damaged by rough-handling resulting in damage to the plant as well as further inconsistency in image quality.

Therefore, there is an unmet need for a novel imaging system that can provide consistent phenotyping images of a large number of plants and their associated leaves to be used for high precision agriculture and phenotyping studies.

SUMMARY

An imaging system for providing consistent images of leaves of plants is disclosed. The system includes a housing. The housing is divided into an upper case and a lower case, wherein the lower case is articulable with respect to the upper case via an imaging chamber articulation mechanism from i) an open state to ii) a closed state. The articulable space between the upper case and the lower case forms an imaging chamber wherein the imaging chamber is configured to be dark when the imaging chamber articulation mechanism is in the closed state. The system also includes a camera disposed within the upper case, wherein the camera is articulable along a first axis within the upper case via a linear actuator from i) an initial position to ii) an end position. The system also includes a light box disposed in the lower case housing one or more light sources. The system also includes a controller. The controller is configured to articulate the lower case to the open state thus configured to allow a leaf of a plant in between the lower case and the upper case within the imaging chamber. The controller is further configured to articulate the lower case to the closed state, activate the one or more light sources, actuate the linear actuator to thereby linearly move the camera within the upper case from the initial position to the end position, obtain images from the camera while the linear actuator moves the camera, re-actuate the linear actuator to thereby linearly move the camera within the upper case from the end position to the initial position. Additionally, the controller is configured to re-articulate the lower case to the open state, thus allowing removal of the leaf.

A method for providing consistent images of leaves of plants, is disclosed. The method includes selecting a leaf of a plant to be imaged. The method also includes articulating a lower case of a housing with respect to an upper case of the housing via an imaging chamber articulation mechanism from i) a closed state to ii) an open state. The articulable space between the upper case and the lower case forms an imaging chamber wherein the imaging chamber is configured to be dark when the imaging chamber articulation mechanism is in the closed state. The method also includes placing the leaf of the plant within the imaging chamber and articulating the imaging chamber articulation mechanism to the closed state. Furthermore, the method includes activating one or more light sources disposed in a light box disposed in the lower case and actuating a linear actuator to thereby linearly move a camera disposed within the upper case from i) an initial position to ii) an end position. The method further includes obtaining images from the camera while the linear actuator moves the camera and re-actuating the linear actuator to thereby linearly move the camera within the upper case from the end position to the initial position. Additionally, the method includes re-articulating the lower case to the open state, and removing the leaf.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel imaging system is disclosed herein that can provide consistent phenotyping images of a large number of plants and their associated leaves to be used for high precision agriculture and phenotyping studies. The novel imaging system includes a single leaf imaging system and a plant imaging system. The leaf imaging system images the leaf in a closed imaging chamber with a hyperspectral or multispectral camera after a robot arm manipulates the leaf into the chamber. The plant imaging system images the entire plant with a hyperspectral or multispectral camera while the ambient light is blocked off. A GPS module and a micro-controller are mounted the imaging system. The controller processes the image and uploads the predicted plant health parameters to a remote server together with the geolocation and time stamp data of the images. The remote server monitors plant health over a large area with timelines at farm-level, plot-level, or county level.

Towards this end, an imaging system 100 is disclosed. The imaging system 100 as further described below is capable of inserting a leaf into an imaging chamber and providing a consistent environment for imaging followed by obtaining a hyperspectral or multispectral image followed by releasing the leaf without harming the plant.

A hyperspectral image includes a large number (in hundreds) of color bands. A hyperspectral imaging system uses a grating (similar to a Newton's prism) to spread different colors into different directions, so the different colors end up at different locations on a Charge-coupled device (CCD) or a complementary metal oxide semiconductor (CMOS) sensor, thereby measuring different colors with different pixels on the camera sensor. A multispectral image has typically 4-10 color bands resulting from light emitting diodes (LEDs) of different colors in the imaging chamber. By alternating through these LEDs (i.e., turn on one color, and keep all the other colors off) and take one shot for each color and obtaining different images therefrom, and eventually combine all the frames of different colors into one multispectral image. In both cases, a scanning approach is used to scan the imaging area line-by-line.

Figure 1:
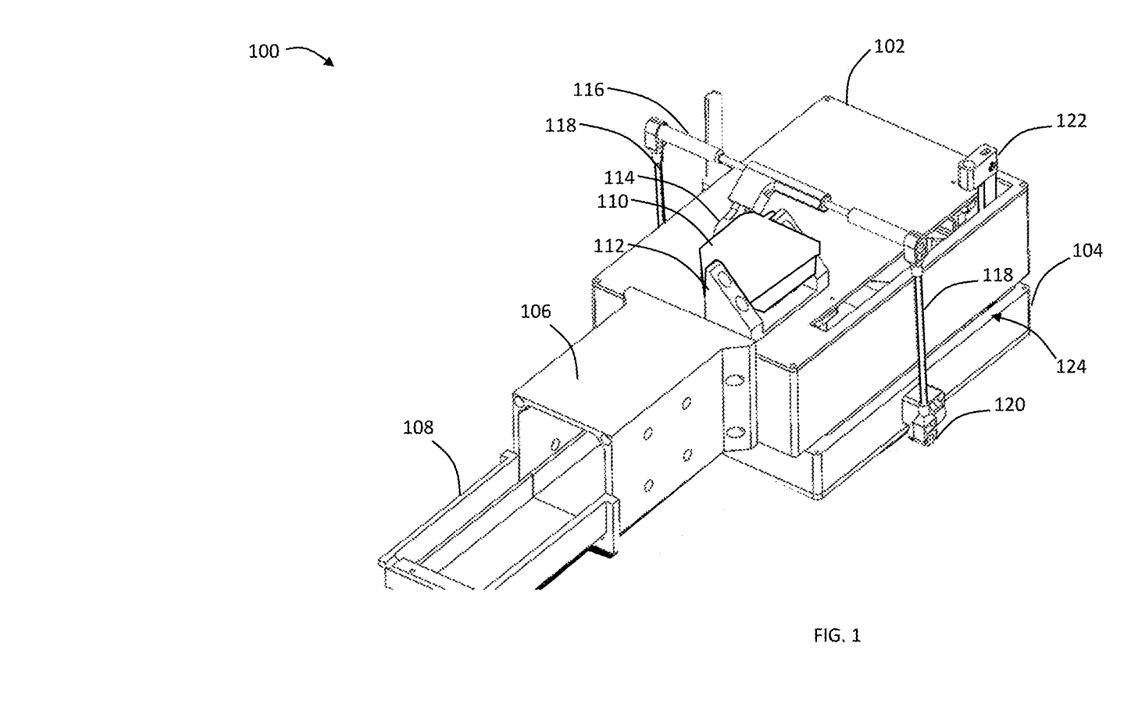
FIG. 1 is a perspective view of an imaging system according to the present disclosure which includes an upper case and a lower case adapted to articulate with respect to the upper case.
Figure 2:
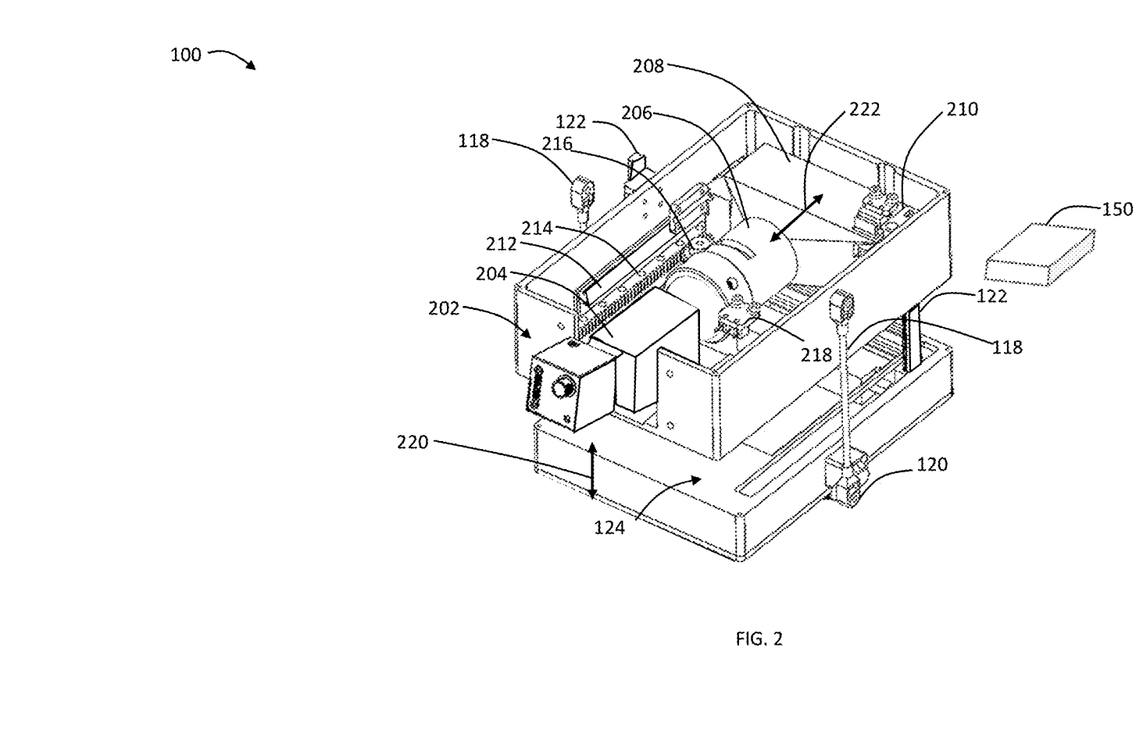
FIG. 2 is a perspective view of the imaging system of FIG. 2 shown with top of the upper case removed to reveal the components within the upper case.

Referring to FIG. 1, the imaging system 100 according to the present disclosure is described. FIG. 1 is a perspective view of the imaging system 100 which includes an upper case 102 and a lower case 104 adapted to articulate with respect to the upper case 102. The imaging system 100 includes a camera housing 106 within which a camera 202 shown in FIG. 2 is disposed. The camera housing 106 terminates to a camera tray 108 adapted to house various electronics accompanied with the camera 202. A servo motor 110 is attached to motor brackets 112 which are firmly attached to the upper case 102. The servo motor 110 is adapted to rotate a first arm 114. The servo motor 110 can be a stepper motor, an alternating current (AC) motor, a direct current (DC) motor, or a variety of other motors and motor-drive controls known to a person having ordinary skill in the art. The first arm 114 is coupled to a second arm 116 which is coupled to a pair of third arms 118 that are coupled to the lower case 104 via bearings 120. The combination of the servo motor, the first arm 114, the second arm 116, the pair of third arms 118, and the bearings 120 allow rotational movement of the servo motor 110 to be converted to horizontal and vertical articulation of the lower case 104 with respect to the upper case 102 via a slider-crank mechanism, known to a person having ordinary skill in the art. The speed of the slider-crank mechanism is much faster than a simple linear actuator because the angle of the servo motor 110 can be controlled by a pulse width modulation (PWM) signal or using a stepper motor based on a digital input. While not shown, a limit bumper can provide a limit for vertical travel of the lower case 104 with respect to the upper case 102. A pair of guides 122 provide motion guidance for the lower case 104. In FIG. 1, an imaging chamber 124 is shown in the collapsed position (i.e., the lower case 104 has articulated with respect to the upper case 102).

Referring to FIG. 2, a perspective view of the imaging system 100 is shown with top removed to reveal the components within the upper case 102. As discussed above, the upper case includes a camera 202 which includes a camera base 204 and a lens assembly 206. The lens assembly is optically coupled to a mirror housing 208 adapted to convey light from the imaging chamber 124 to the camera 202. It should be appreciated that a plurality of LEDs (not shown) may be disposed in the lower case 104 configured to provide light with different wavelengths (i.e., colors) to the mirror housing 208 through a leaf 150 that is positioned in the imaging chamber 124 for light travelling through the leaf 150. Additionally, one or more LEDs (not shown) again with different wavelengths (i.e., colors) may be disposed in the upper case 102 adapted to shine light at the leaf 150 for reflection off the leaf 150 and onto the mirror housing.

As described above, the imaging system 100 is based on scanning line-by-line. Towards this end a linear actuator is employed capable of moving the camera 202 and the mirror housing 208 along a horizontal plane 222. According to one embodiment, a rack and pinion system known to a person having ordinary skill in the art is employed to generate said articulation, however, other systems can be used including a lead screw, a belt drive, or a chain drive. On a horizontal rail 212 a rack 214 is mounted. The rack 214 includes a plurality of gear teeth (e.g., 20 teeth with a pitch diameter of 16 mm). A pinion 216 with circular gear teeth coupled to an actuator (not shown, e.g., a micro metal gear motor with a 1000:1 gear ratio with physical dimension of 29.5 mm×10 mm×12 mm (length×width×height) and a weight of 10.5 grams, producing a maximum torque of 11 kg·cm which is sufficient to cause linear movement of the aforementioned components) is adapted to engage with the teeth on the rack 214 and cause the assembly of the camera 202 and the mirror housing 208 to move along the direction 222 for the aforementioned line-scanning. A limit switch 210 is adapted to electronically engage the actuator (not shown) of the pinion 216 to stop the linear motion thereby avoiding excess linear travel. The camera 202 includes a camera connector 218 which provides electronic signal associated with hyperspectral or multispectral images. The camera connector 218 may provide these electronic signals via a wired connection (e.g., a ribbon cable) or based on a wireless protocol, in each case to a computing device further described below. The vertical articulation of the lower case 104 with respect to the upper case 102 is shown via the double arrow 220.

Figure 3:
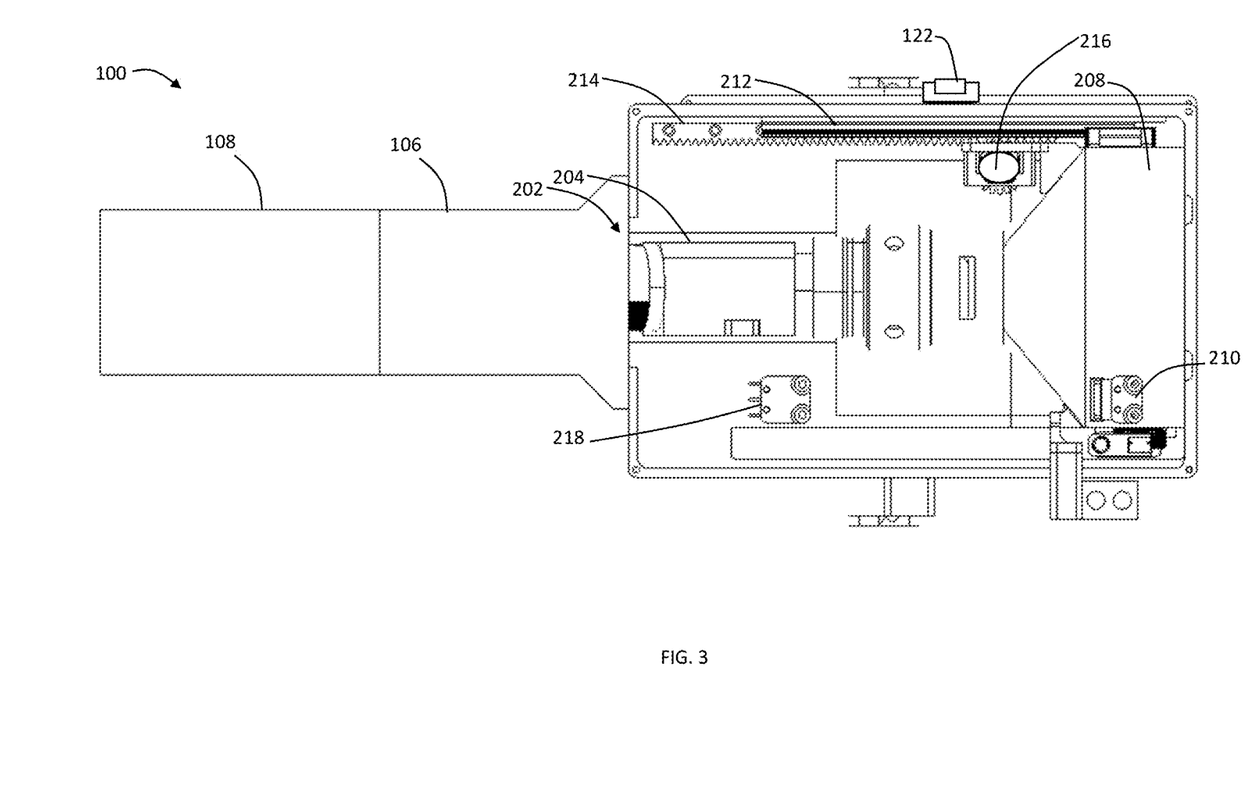
FIG. 3 is a top view of the imaging system of FIG. 1 with top of the upper case removed to better elucidate the internal components.

Referring to FIG. 3, a top view of the imaging system 100 is provided, again with top of the upper case 102 removed to better elucidate the internal components. In FIG. 3, it is better reveled how the camera base 204 is adapted to enter the camera housing 106 during the articulation of the assembly of the camera 202 and the mirror housing 208.

Figure 4:
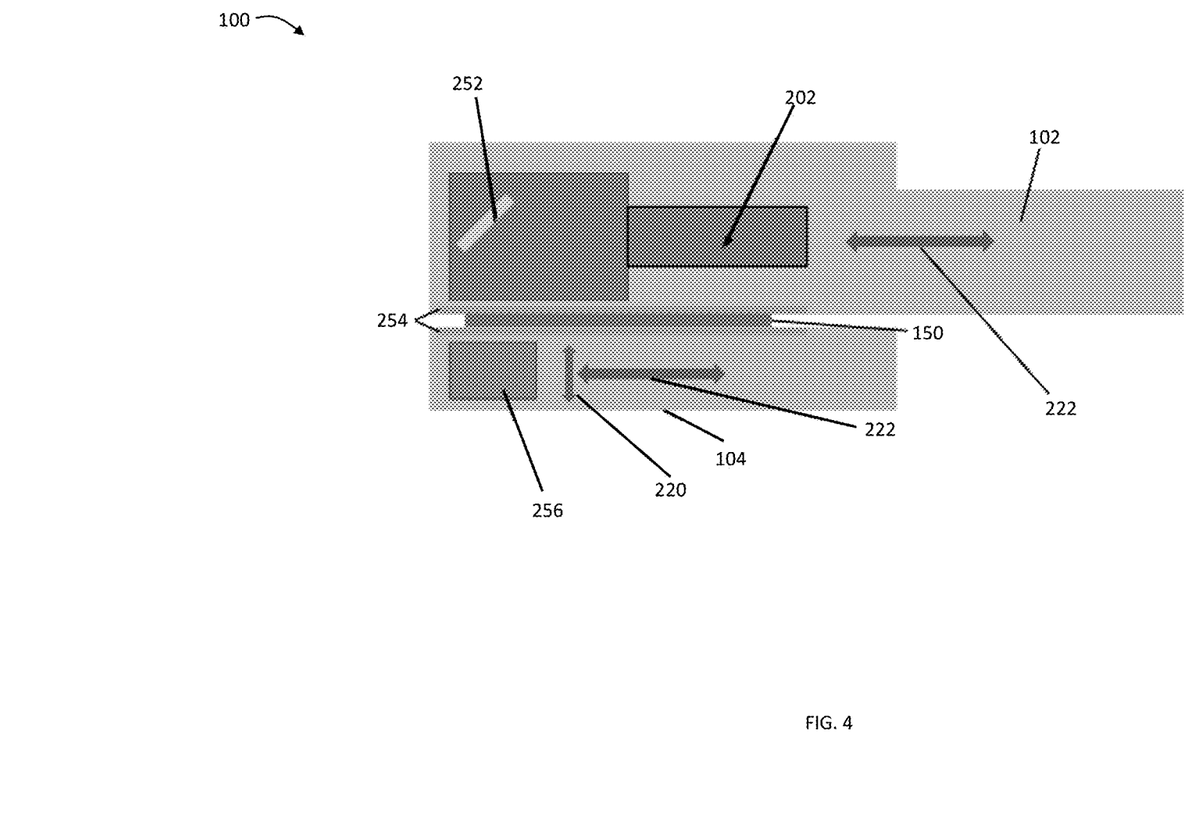
FIG. 4 is a schematic of the imaging system of FIG. 1.

Referring to FIG. 4, a schematic of the imaging system 100 is shown. This figure reveals the position of a mirror 252 within the mirror housing 208 as well a light box 256 in the lower case 104 adapted to house the plurality of above-described LEDs (not shown) and/or halogen lights. Two glass plates 254 are provided (one coupled to the upper case 102 and one coupled to the lower case 104). While not shown, a linear guideway mounting vertically couples the camera 202 to the light box 256. The is linear guideway (not shown) allows the light box 256 and the camera 202 to move in concert with one-another, horizontally. Thus, the light box 256 is adapted to horizontally move in concert with the camera 202 in order to enhance illumination of the leaf 150 as the camera 202 moves within the upper case 202. These glass plates are adapted to provide a consistent imaging environment for the hyperspectral or multispectral imaging while allowing light to travel from the light box 256 through the leaf 150 and to the mirror 252. The material for the glass plates can be anything that is translucent, e.g., glass, plexiglass, or other such materials known to a person having ordinary skill in the art. It should be appreciated that while vertical distance in FIG. 3 between the glass plates 254 and the leaf 150 appear to be minimal (i.e., it appears that the glass plates 254 are touching the leaf 150), as described above a limit switch (not shown) can be implemented to limit this vertical relationship to avoid contact with the leaf 150. In one embodiment, the vertical distance is maintained at a minimum of the range of between about 3 mm to about 10 mm (i.e., between the two glass plates 254). It should be appreciated that the space within the imaging chamber 124 is dark to prevent optical noise for improved consistency. Therefore, blinds (not shown) are employed all around the imaging chamber 124 in order to darken the space within when the lower case 104 is in the articulated position with respect to the upper case 102 as shown in FIG. 1.

In hyperspectral imaging according to the present disclosure, the red edge (RE, 670-780 nm) in the spectrum is used to model the plant stress, nutrient content, and chlorophyll content. The imaging system 100 needs to operate in both visible and near-infrared (NIR) bands. The operating range for the imaging system 100 is between 450 nm to 900 nm. The camera 202 also includes an imaging sensor (not shown).

Figure 5:
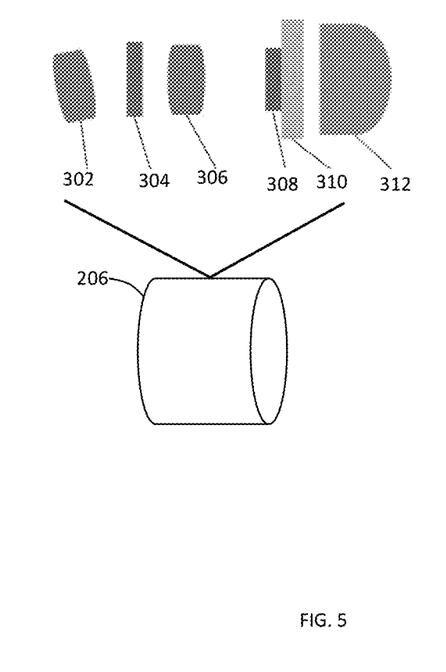
FIG. 5 is an exploded view is provided for a lens assembly used in the imaging system of FIG. 1.

Referring to FIG. 5, an exploded view is provided for the lens assembly 206. The lens assembly 206 includes focusing lens 302, a grating 304, one or more collating lenses 306, one or more filters 308, a slit 310, and a collecting lens 312. These components are further described below.

The role of the diffraction grating 304 is to separate the incoming polychromatic light into monochromatic light. The diffraction grating 304 is a transmission grating (e.g., GT13-03 from THORLABS INC). The grating 304 has 300 grooves per millimeter with a groove angle of 17.5 degrees. The physical dimensions of the grating are 12.7 mm×12.7 mm. The transmittance of the grating has a range of 38% to 74% between the 450 nm and 900 nm light. The diffraction angle of the grating is 11.35 degrees based on Equation 1, below:

$$n\lambda = d(\sin\theta + \sin\dot\theta) \quad \text{Equation 1}$$

where n is the diffraction order,
$\lambda$ is the wavelength of the monochromatic light,
d is the groove spacing,
$\theta$ is the groove angle, and
$\dot\theta$ is the diffraction angle.

Since only the first-order diffraction pattern is needed for the imaging system 100, a filter 308 is added to remove the light with a wavelength under 440 nm because it can generate a second-order diffraction pattern. The filter 308 used in the imaging system 100 is a long-pass filter (e.g., 62-975 from EDMUND OPTICS). The transmission efficiency of the filter 308 is over 91% between the range of 458 nm to 1600 nm.

The slit 310 inside the imaging system 100 acts as an aperture in a traditional RGB camera, limiting the amount of light passing through. The slit 310 (e.g., S50RH from THORLABS INC.) has a physical dimension of 50 microns wide and 3 mm long. Since the slit 310 is a rectangular shape, the slit only allows one line of light through.

There are three lenses used in the imaging system 100: the collecting lens 312, the collating lens 306, and the focusing lens 302. The collecting lens 312 focuses the light transmitted through (or reflected from) the leaf onto the slit 310. The collecting lens 312 has a 4 mm focal length which is specifically designed for soybean leaves, however, for other plant leaves, e.g., corn, other collecting lenses may be used. The purpose of the collating lens 306 is to convert the light exiting the slit into parallel light so the light can be diffracted using the diffraction grating 304. The purpose of the focusing lens 302 is to focus the monochromatic light from the diffraction grating 304 onto an imaging sensor (not shown). For both the collating lens 312 and the focusing lens 302, an achromatic doublet (not shown, e.g., #63-720 from EDMUND OPTICS) was used with a focal length of 30 mm and a diameter of 10 mm.

The imaging sensor (not shown) that was used in the imaging system 100 is a monochrome camera (e.g., BFLY-U3-05S2M-CS from TELEDYNE FLIR). A monochrome camera is needed because the camera 202 is a line scanning camera. For each pixel in the image, it represents the intensity of a wavelength at a certain position on the line. The imaging sensor is equipped with a SONY CCD with a global shutter. The imaging sensor uses USB 3.1 for power and data transfer as discussed above with respect to the camera connector 218.

As described above, the imaging system 100 encloses the leaf 150 in the imaging chamber 124 which is a dark chamber. The light source of the imaging system 100 is the lightbox 256 on the lower side of the leaf which is installed with two 12 W halogen lights. Halogen lights are chosen because the light it emits covers a wide range of wavelengths from visible to infrared (IR) with a very smooth spectrum. Since the camera 202 is a line scanning camera, the lightbox 256 is designed to only illuminate a narrow and long section of the leaf 150. A TEFLON sheet covers the outlet of the lightbox 256 to diffuse light across the entire illuminating section. The lightbox 256 was made with aluminum with a mirror-like finish inside. The mirror-like finish allows the light to reflect effectively inside the lightbox which increases the brightness of the light output.

Figure 6:
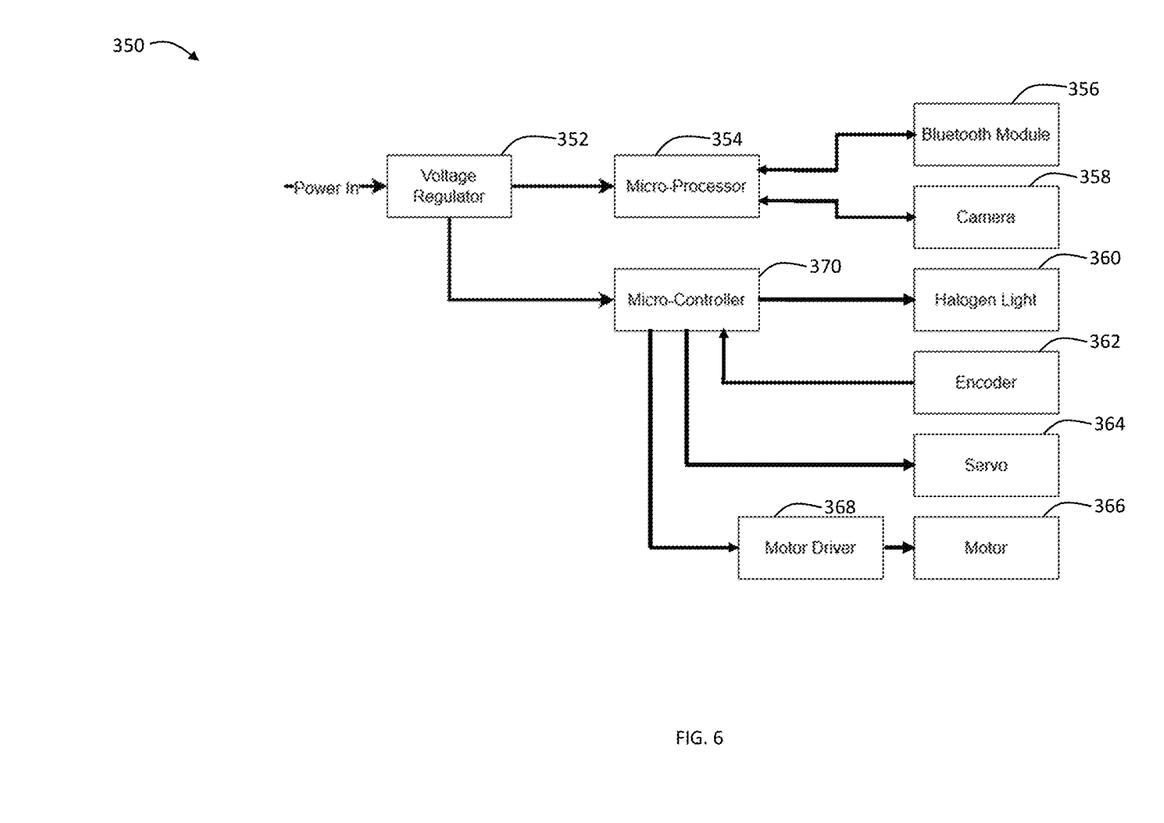
FIG. 6 is a block diagram for an electronics assembly of the imaging system according to the present disclosure.

Referring to FIG. 6, a block diagram is shown for an electronics assembly 350 of the imaging system 100. The electronics assembly 350, a voltage regulator 352, a microprocessor 354, and a micro-controller 370. The voltage regulator 352 regulates input voltage (shown as Power In) of 24 V to 12 V and 5 V. The microprocessor 354 interfaces with the camera 202 (shown in FIG. 6 as 358), micro-controller 370, and a communication (e.g., BLUETOOTH®) module 356 which is adapted to communicated with an external device, e.g., a smartphone. The microprocessor 354 also processes the incoming image data from the camera 202 into hyperspectral images. The micro-controller 370 receives commands from the microprocessor to actuate the mechanisms described above and lights inside the light box 256.

The voltage regulator 352 accepts 24 VDC as input voltage, e.g. from a battery, for use for the components listed in FIG. 6. Since the battery voltage changes over time, two voltage regulators (not shown) are utilized to provide steady voltage for the components shown in FIG. 6. One of the voltage regulators (not shown) transforms the 24 VDC to 12 VDC for powering the halogen light. Another voltage regulator transforms the power from 24 VDC to 5 VDC to power the microprocessor, micro-controller, and all the associated peripherals. The servo motor 110 uses the 24 V incoming power (Power In).

The microprocessor 354 handles the computation and storage of data, communication with the external device (e.g., a smartphone) over BLUETOOTH® utilizing the communication (e.g., BLUETOOTH®) module 356, and sends commands to the micro-controller 370. An example of the microprocessor is RASPBERRY PI 4 by RASPBERRY PI FOUNDATION in association with BROADCOM. The RASPBERRY PI 4 has 4 GB of RAM to temporarily store image data from the imaging sensor during scanning. The microprocessor 354 may have an integrated communication (e.g., BLUETOOTH®) module (thus replacing the stand-alone communication (e.g., BLUETOOTH®) module 356) or via the communication (e.g., BLUETOOTH®) module 356 to send scan information and receive commands from the externa device, e.g., a paired smartphone which is a user interface of the imaging system 100. The microprocessor communicates with the micro-controller via a serial communication protocol, e.g., Universal Asynchronous Receiver-Transmitter (UART).

The micro-controller 370 is responsible to actuate all the articulation mechanisms as well as the illumination lights. An example of the micro-controller is an ARDUINO NANO made by ARDUINO. This micro-controller was chosen because it has hardware PWM which provides a clean signal to control the motor of the pinion 216 (shown in FIG. 6 as 366) and the servo motor 110 (shown in FIG. 6 as 364) when under load. The motor 366 is driven by a motor drive 368 which is coupled to the micro-controller 370. In contrast, the PWM signal from the RASPBERRY PI 4 is simulated using software that is not reliable under load, and it also requires significant computation time to generate the PWM signal. The micro-controller controls the motor of the pinion 216 (FIG. 6 as 366) by using an H-bridge motor controller, known to a person having ordinary skill in the art, which uses two PWM signals to control the speed and direction of the motor. The microprocessor 354 may also have hardware interrupts which are important for sensing encoder signals generated by encoders 362 which provide positional information at high speed. According to one embodiment, in the motor of the pinion 216 (shown in FIG. 6 as 366), a magnetic encoder that uses two hall-effect sensors provide positional information of the motor. This encoder has a resolution of 12000 counts per revolution which means the encoder has a 0.004 mm special resolution given the motor geometry. To limit the range of the scanning area, two limit switches (one is shown at one end of the scanning as the limit switch 210, while the second one is positioned at end of scanning but not shown) are used and connected to the micro-controller. Halogen lights 360 are controlled by the micro-controller 370 using a p-channel MOSFET (e.g., IRF520 made by STMICROELECTRONICS) since halogen lights draw about 2A of current when activated.

In operation, an external device, e.g. an Android smartphone is interfaced with the electronic assembly 350 via the communication (e.g., BLUETOOTH®) interface for previewing the hyperspectral or multi-spectral images taken by the imaging system 100.

Figure 7:
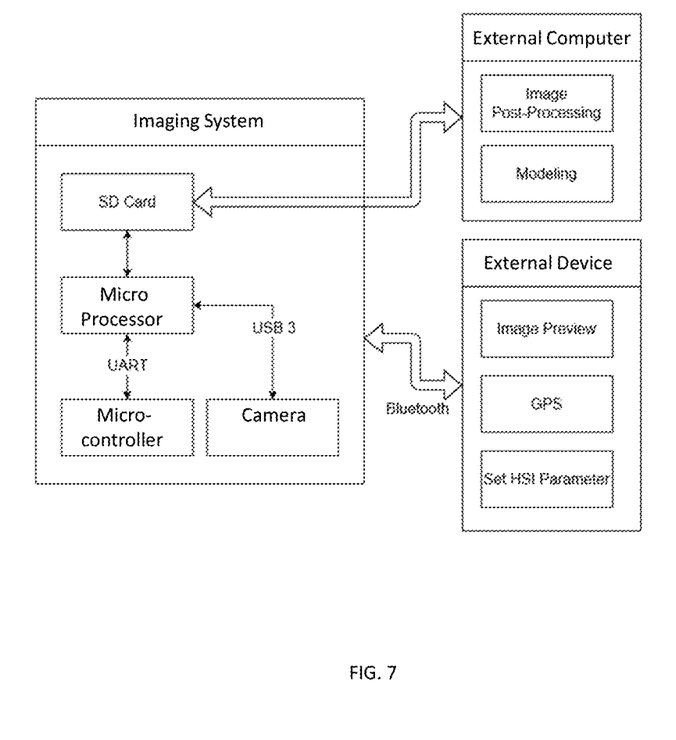
FIG. 7 is a block diagram which shows how data flows between different components of the electronic assembly of FIG. 6.
Figure 8:
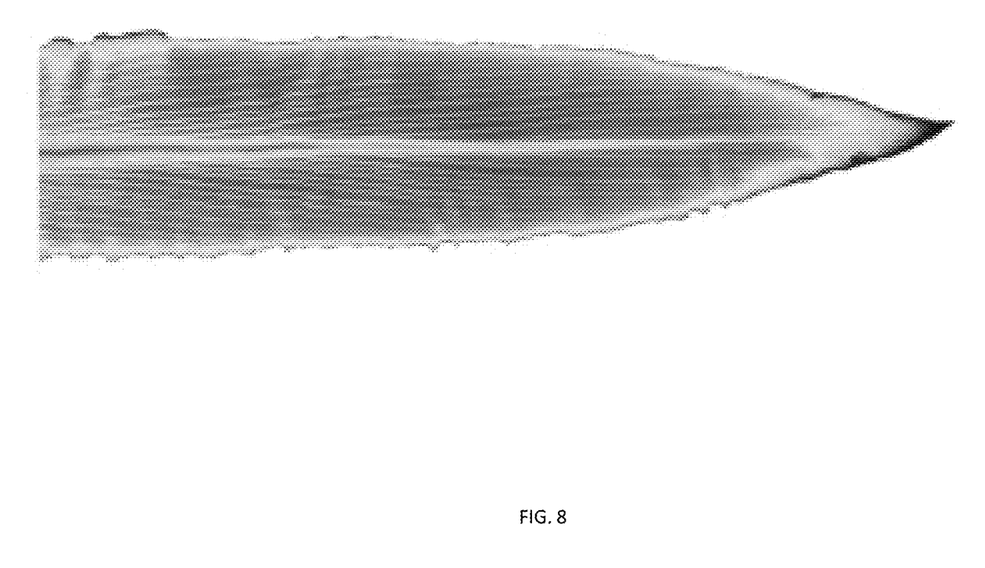
FIG. 8 is an example of a Normalized Difference Vegetation Index (NDVI) heatmap of a soybean leaf which shows the distribution of NDVI values is not uniform.

Referring to FIG. 7, a block diagram shows how the data flows between different components of the electronic assembly 350. The imaging system 100 can be triggered to start scanning by using a push-button for manual operation or a relay for autonomous operation. The microprocessor 354 initializes the scanning by sending a command to the micro-controller 370 to first close the imaging chamber by causing the activation of the servo motor, and then start spinning the motor of the pinion 216. The motor runs continuously until reaching one of the two limit switches 210. After the motor has started spinning, the microprocessor 354 begins acquiring images from the camera 202 for each line until the end of the travel as indicated by the limit switch (not shown). As soon as an image has been received, the microprocessor 354 stores the image in memory, e.g., random access memory (RAM) for later processing after the scanning has been completed. Once the scanning has been completed, the micro-controller reverses the motor of the pinion 216 until the limit switch 210 provides a signal indicating return to its original position. Meanwhile, the microprocessor 354 processes the data by organizing the images into a single hypercube. The microprocessor 354 also generates a Normalized Difference Vegetation Index (NDVI) heatmap for displaying on the external device, e.g., a smartphone. The user can then choose to save or discard the data on the external device. The entire image hypercube data is saved on a secure digital (SD) card installed on the microprocessor 354. FIG. 8 provides an example of the NDVI heatmap of a soybean leaf which shows the distribution of NDVI values is not uniform.

Those having ordinary skill in the art will recognize that numerous modifications can be made to the specific implementations described above. The implementations should not be limited to the particular limitations described. Other implementations may be possible.

The invention claimed is:
1. An imaging system for providing consistent images of leaves of plants, comprising:
    a housing, the housing divided into an upper case and a lower case, wherein the lower case is articulable with respect to the upper case via an imaging chamber articulation mechanism from i) an open state to ii) a closed state, an articulable space between the upper case and the lower case forms an imaging chamber wherein the imaging chamber is configured to be dark when the imaging chamber articulation mechanism is in the closed state;

a camera disposed within the upper case, wherein the camera is articulable along a first axis within the upper case via a linear actuator from i) an initial position to ii) an end position;

a light box disposed in the lower case housing one or more light sources; and a controller configured to:

a) articulate the lower case to the open state thus configured to allow a leaf of a plant in between the first lower case and the upper case within the imaging chamber, b) articulate the lower case to the closed state, c) activate the one or more light sources, d) actuate the linear actuator to thereby linearly move the camera within the upper case from the initial position to the end position, e) obtain images from the camera while the linear actuator moves the camera, f) re-actuate the linear actuator to thereby linearly move the camera within the upper case from the end position to the initial position, and g) re-articulate the lower case to the open state, thus allowing removal of the leaf, the imaging chamber articulation mechanism is a slider-crank mechanism including a servo motor coupled to the upper case, a plurality of arms coupling the servo motor to the lower case, wherein the plurality of arms transform rotational motion of the servo motor to linear motion of the lower case with respect to the upper case.

2. The imaging system of claim 1, wherein camera is a hyperspectral camera capable of generating hyperspectral images.

3. The imaging system of claim 1, wherein camera is a multispectral camera capable of generating multispectral images.

4. The imaging system of claim 1, wherein the linear actuator is a rack-and-pinion system.

5. The imaging system of claim 4, wherein the rack-and-pinion system includes a rack having a plurality of linearly disposed teeth disposed along a rail and a pinion having a plurality of circularly disposed teeth engaged with the linearly disposed teeth of the rack, wherein the pinion rotates via a pinion motor.

6. The imaging system of claim 5, wherein the pinion motor is one of an alternating current (AC) motor, a direct current (DC) motor, and a stepper motor.

7. The imaging system of claim 1, wherein the linear actuator is a lead screw system wherein a motor is coupled to a screw interfacing a nut where the nut is coupled to the camera.

8. The imaging system of claim 1, wherein the linear actuator is a belt drive or a chain drive, wherein the camera interfaces with a gear coupled to a motor via a belt or a chain.

9. The imaging system of claim 1, wherein the servo motor is one of an alternating current (AC) motor, a direct current (DC) motor, and a stepper motor.

10. A method for providing consistent images of leaves of plants, comprising:

selecting a leaf of a plant to be imaged;

articulating a lower case of a housing with respect to an upper case of the housing via an imaging chamber articulation mechanism from i) a closed state to ii) an open state, an articulable space between the upper case and the lower case forms an imaging chamber wherein the imaging chamber is configured to be dark when the imaging chamber articulation mechanism is in the closed state;

placing the leaf of the plant within the imaging chamber;

articulating the imaging chamber articulation mechanism to the closed state;

activating one or more light sources disposed in a light box disposed in the lower case;

actuating a linear actuator to thereby linearly move a camera disposed within the upper case from i) an initial position to ii) an end position;

obtaining images from the camera while the linear actuator moves the camera;

re-actuating the linear actuator to thereby linearly move the camera within the upper case from the end position to the initial position;

re-articulating the lower case to the open state; and removing the leaf, the imaging chamber articulation mechanism is a slider-crank mechanism including a servo motor coupled to the upper case, a plurality of arms coupling the servo motor to the lower case, wherein the plurality of arms transform rotational motion of the servo motor to linear motion of the lower case with respect to the upper case.

11. The method of claim 10, wherein camera is a hyperspectral camera capable of generating hyperspectral images.

12. The method of claim 10, wherein camera is a multispectral camera capable of generating multispectral images.

13. The method of claim 10, wherein the linear actuator is a rack-and-pinion system.

14. The method of claim 13, wherein the rack-and-pinion system includes a rack having a plurality of linearly disposed teeth disposed along a rail and a pinion having a plurality of circularly disposed teeth engaged with the linearly disposed teeth of the rack, wherein the pinion rotates via a pinion motor.

15. The method of claim 14, wherein the pinion motor is one of an alternating current (AC) motor, a direct current (DC) motor, and a stepper motor.

16. The method of claim 10, wherein the linear actuator is a lead screw system wherein a motor is coupled to a screw interfacing a nut where the nut is coupled to the camera.

17. The method of claim 10, wherein the linear actuator is a belt drive or a chain drive, wherein the camera interfaces with a gear coupled to a motor via a belt or a chain.

18. The method of claim 10, wherein the servo motor is one of an alternating current (AC) motor, a direct current (DC) motor, and a stepper motor.

* * * * *